United States Patent [19]

Lupton et al.

[11] 4,291,019

[45] Sep. 22, 1981

[54] VACCINE FOR INFECTIOUS BOVINE RHINOTRACHEITIS

[75] Inventors: Harold W. Lupton, Walkersville, Md.; David E. Reed, Ames, Iowa

[73] Assignee: Iowa State University Research Foundation, Inc., Ames, Iowa

[21] Appl. No.: 146,141

[22] Filed: May 2, 1980

Related U.S. Application Data

[63] Continuation-in-part of Ser. No. 55,821, Jul. 9, 1979, abandoned.

[51] Int. Cl.³ ............................................. A61K 39/265
[52] U.S. Cl. ..................................... 424/89; 435/235; 435/236; 435/238; 435/239
[58] Field of Search .................... 424/89; 435/235–239

[56] References Cited

U.S. PATENT DOCUMENTS 4,158,054  6/1979  Furminger et al. .................. 424/89

OTHER PUBLICATIONS

Lupton et al., Am. J. Vbt. Res., 41 (3): 383–390, Mar. 1980, Evaluation of Experimental Subunit Vaccines for Infectious Bovine Rhinotracheitis.
Vester Gaard et al., J. Virol. 24 (1): 82–90, Oct. 1977, Crossed Immunoelectrophoretic Studies of the Solubility and Immunogenicity of Herpes Simplex Virus Antigens.
Cappel Arch Virol. 52: 29–35, (1976), Comparison of the Humoral and Cellular Immune Responses After Immunization with Live, Uninactivated Herpes Simplex Virus and a Subunit Vaccine and Efficacy of these Immunizations.
Kaplan et al., Progr. Med. Virol. 21: 1–12 (1975), Excretion of Specific Glycoproteins by Cells Infected with Herpes Simplex Virus, Types 1 and 2.
Buxton et al., Animal Microbiology, vol. 2, Blackwell Sci. Pub. Ltd., Oxford, UK., (1977), pp. 407–427, 737–740, 745–747.

*Primary Examiner*—Shep K. Rose

[57] ABSTRACT

A vaccine for infectious bovine rhinotracheitis (IBR) is prepared by non-ionic detergent extraction of IBR virus infected cells. The extracted viral envelope protein can be prepared in injectable dose form by combination with an oil-type adjuvant. The vaccine produces a high level of antibody response, and is capable of eliminating virus shed for animals infected after immunization.

8 Claims, No Drawings

VACCINE FOR INFECTIOUS BOVINE RHINOTRACHEITIS

CROSS-REFERENCE

This application is a continuation-in-part of copending application Ser. No. 55,821, filed July 9, 1979, now abandoned.

BACKGROUND AND PRIOR ART

Infectious bovine rhinotracheitis (IBR) was first recognized as a distinct disease of cattle during the 1950's. Consistent with the characteristics of other herpesviruses, IBR virus (IBRV) replicates in a wide range of cell types and produces diverse disease manifestations which include respiratory tract disease, conjunctivitis, vulvovaginitis, abortion, balanoposthitis, meningoencephalitis, alimentary tract disease and fatal systemic infection. However, IBR is known mainly as a respiratory tract disease characterized by tracheitis, rhinitis, and fever. IBR infection is the most commonly diagnosed cause of abortion in pregnant cattle. See Kirkbride et al, *J. Am. Vet. Med. Assoc.*, 162, 556-560 (1973). The virus is readily transmitted and has worldwide distribution. Some cattle develop a latent infection, which can be reactivated.

Control of IBR is based largely on vaccination, and a number of different kinds of IBR vaccines have been developed. See Kahrs, *J. Am. Vet. Med. Assoc.*, 171, 1055-1060 (1977). These include parenteral and intranasal vaccines, both of which use live attenuated IBRV. The parenteral vaccines, which are usually administered intramuscularly, may cause abortion in pregnant cattle, and are therefore contraindicated for pregnant cattle. Further, vaccination of suckling calves which are nursing pregnant cattle may cause abortion due to the shedding of virus by the vaccinated calves. Intranasal vaccines are safer in these respects, and are capable of producing humoral antibodies at titers comparable with those of intramuscular vaccines. However, there are problems associated with administration of intranasal vaccines. Head restraint is required, and care must be taken to administer the vaccine deeply into both nostrils. There is a tendency for vaccinated animals to blow the vaccine out when they snort after vaccination.

The degree of efficacy of prior art vaccines is variable, and the duration of protection is limited. In general, it is believed that intramuscular vaccination gives protection of longer duration than intranasal vaccination. With intranasal vaccination, conservative practice dictates annual revaccination, while at least occasional revaccination is recommended with the intramuscular vaccines. Inactivated IBR vaccines have also been developed, but there is controversy about their effectiveness. Annual revaccination is recommended. Further disadvantages of inactivated vaccines include concern for fatal hypersensitivity reaction (anaphylaxis) and nonfatal urticaria.

Heretofore no subunit IBR vaccine has been reported. However, a subunit approach to the preparation of some other virus vaccines has been explored. See, for example, Rubin et al, *Progr. Med. Virol.*, 21, 144-157 (1975). Cappel has reported experiments with a subunit vaccine of herpes simplex virus in rabbits. *Arch. Virol.* 52, 29-35 (1976). The subunit vaccine was found as effective as immunization with live or U.V inactivated herpes simplex virus. Similarly, Cox et al have reported experiments with a subunit vaccine for human rabies. *Infect. and Immun.*, 16, 753-754 (1977). Both Cappel and Cox et al worked with non-ionic detergent extracts of the virions, since it is known that non-ionic detergents are capable of solubilizing envelope glycoproteins of viruses. See Helenius et al, "Solubilization of Membranes by Detergents", *Biochem. et Birphys. Acta*, 415, 29-79 (1975). However, Sokal stated as a general rule that subunit vaccines containing soluble antigens would be epxected to provide a specific immunogenicity or specific protective action which is markedly lower than that of virion vaccines. Sokal, *Vaccines of the Future: Immunogenicity of Viral Components*, Chapt. 9, pp. 129-135, in Viruses and Immunity, Koprowski and Koprowski, 1975, Academic Press, Inc..

SUMMARY OF INVENTION

This invention is based in part on the discovery of the means for producing IBR vaccines giving markedly higher antibody responses than any previous experimental or commercial IBR vaccines. Further, the vaccines prepared in accordance with the present invention are capable of producing higher antibody responses than those found in cattle which have recovered from natural IBR infections.

The vaccines of the present invention are prepared from virulent IBRV, such as field isolates of IBRV or substantially unattenuated IBRV. The IBR virus in its natural or virulent form is propagated in a cell-medium mixture capable of promoting the multiplication of the virus. After propagation, the infected cells are separated from the mixture, and are extracted with an aqueous solution of a non-ionic detergent to obtain an aqueous solution of the antigenic protein. The non-solubilized residue is separated from the supernatant solution, which is then employed as the antigenic ingredient of the vaccine. The soluble antigen in aqueous solution if preferably combined with a suitable adjuvant to provide parenteral vaccine in injectable dose form. Oil-type adjuvants are preferred, such as Freund's Incomplete Adjuvant.

At an effective dose level in combination with a suitable adjuvant, a level of antibody response can be obtained which confers immunity to the disease and also prevents the development of an IBR infection. This is indicated by the fact that vaccinated animals when challenged with live virulent IBRV do not shed virus. This finding is most unexpected since virus shed is always found after challenge of calves vaccinated with any existing vaccine, and there are no known literature references suggesting that prevention of IBR virus shed is attainable by vaccination. The vaccinated cattle do not develop lesions or clinical signs of IBR illness.

The vaccines of the present invention can be used in pregnant animals, in suckling calves, and in calves with maternal antibodies. The vaccines are free from active IBR virus, and therefore cannot cause infection or transfer of IBRV. Further, because the vaccines are of limited antigenic composition, serologic tests can be devised to distinguish vaccinates from infected animals. This cannot be done with currently available IBR vaccines. More specifically, the vaccine of the present invention could be used in a local or a national eradication program, because control of virus shedding is essential to controlling virus transmission. Presently available IBR vaccines do not prevent shed of virus or establishment of latent infections.

DETAILED DESCRIPTION

Any virulent strain of infectious bovine rhinotracheitis virus (IBRV) can be used in practicing the present invention. For example, the Cooper strain can be used, which is supplied as an IBR challenge virus by the Veterinary Services Laboratory, U.S.D.A., Ames, Iowa. Virulent IBRV strains can be obtained from other sources, such as the American Type Culture Collection. For example, ATCC No. VR-188 is suitable. Alternatively, field isolates can be collected from IBRV infected cattle, thereby assuring that such isolates are fully virulent. However, such virulent strains can be subjected to a number of in vitro cell passages while retaining virulence, as indicated by the ability to infect cattle and cause clinical signs of IBR, for example, an average temperature elevation of over 103.5° F.

The virulent IBRV is propagated by cell culture. Preferably, bovine cells are employed which are capable of propagating IBR virus to a high titer, such as bovine lung cells, kidney cells, testicle cells, etc. Established lines of bovine cells adapted for in vitro culture can be used, although good results can also be obtained with freshly collected cells. For purposes of the virus propagation, the cells are combined with a suitable nutrient medium, which is adapted to promote the growth of the virus to a high titer. For example, the basal medium may comprise Eagle's minimum essential medium (MEM). To promote viral multiplication, inclusion of fetal calf serum (FCS) is desirable. For example, 10% FCS can be used for growth of the cells, and a 5% FCS level for maintenance of the cells after infection while the virus is multiplying. Within 24 hours after inoculation with the IBRV, the cells have been killed and the propagation of the virus is completed. The desired viral envelope protein is associated with the cell membranes where it has collected before being formed into IBR viral particles.

On completion of the propagation, the cells are preferably separated from the liquid media. In one procedure, this can be accomplished by centrifugation. For example, the cells will be pelleted out of the cell culture medium by centrifugation at $100,000 \times g$ for 60 minutes. The separated cells are then extracted with a non-ionic detergent, which solubilizes the membrane-associated viral envelope protein and inactivates the IBR virus. The cell pellets may be resuspended in water containing the non-ionic detergent for the solubilization. Detergent concentrations of 0.5 to 5% can be used. The non-ionic detergents which have been found effective for solubilizing viral envelope glycoprotein are advantageous. For example, Triton X-100 (octyl phenoxy polyethoxyethanol) can be used. This non-ionic detergent is produced by Rohm & Haas Co., Philadelphia, Pa., and is distributed commercially by Sigma Chemical Co., St. Louis, Mo. Nonidet P 40 is another non-ionic detergent which has been reported in the literature as desirable for selective dissolving of viral envelope protein. Nonidet P 40 is produced by BDH Chemicals Ltd., Poole, England, and distributed in the United States by Gallard-Schlesinger Chemical Mfg. Corp., Carle Place, N.Y.. Such non-ionic detergents solubilize viral envelope protein without appreciable denaturation of the protein.

Contacting of the aqueous detergent solution with the cellular membranes can be prompted by mechanical disruption or dispersion of the cells. For example, the resuspended cells can be passed through a homogenizer or subjected to sonication, thereby promoting the contacting of the non-ionic detergent with the cellular membranes and the IBR virus. Very little of the desired viral envelope protein is obtained from the IBR viral particles themselves, but complete inactivation of the IBR virus is desirable. It is desirable to carry out the contacting at a neutral or slightly alkaline pH to solubilize the viral envelope protein, such as from a neutral pH to Ph 9.0. A suitable buffer can be included in the aqueous solution to maintain the desired pH. The water used for the extraction is preferably sterile deionized water. The extraction can be completed in one to two hours. For example, with homogenization and/or sonication, and continued stirring of the cell suspension in the aqueous detergent, the extraction can be completed in one hour. Preferably, the suspension is maintained at a temperature below 10° C. during the extraction, such as a temperature of about 4° C. On completion of the extraction, the residue of solid material is separated from the supernatant solution of solubilized protein. For example, the separation can be accomplished by centrifugation. The cell debris may be pelleted by centrifugation at $100,000 \times g$ for 60 minutes.

The extract of subviral protein thus obtained can be used directly to prepare vaccines, where, as preferred, it contains a sufficient concentration of protein to permit it to be mixed with an adjuvant to prepare injectable doses of vaccine. The amount used per dose should be effective to prevent IBR disease, either as a single injection or as a sequence of two injections. For example, the extract may contain from 3 to 6 milligrams (mg) of extracted protein solids per milliliter (ml). The injectable dose form of the vaccine may be prepared by mixing equal parts of a suitable adjuvant and the subviral protein extract as obtained (without concentration). While the vaccine (protein extract with adjuvant) may contain from 0.5 to 10 mg/ml of total protein (solids basis), it will usually contain an amount within the range from 1 to 6 mg/ml of the extracted protein. For example, where the dose of the vaccine is to comprise 2 milliliters, the total dose will then comprise from 2 to 12 mg of total protein, such as a total dose of 4 to 8 mg.

If desired, the antigenic protein may be concentrated or recovered prior to preparation of the vaccine, such as by salting out or ultrafiltration. Where the antigenic protein is recovered in solid form, it is preferably resuspended in water at the desired concentration for incorporation in the vaccine. Then, as previously indicated, the solution of viral envelope protein is combined with a suitable adjuvant. Since the antigen is in solution, it is preferred to combine the aqueous solution with an oil-type adjuvant. For example, Freund's Incomplete Adjuvant may be used. This adjuvant may be purchased from a commercial source, such as Difco Laboratories, Detroit, Mich., or it may be prepared by combining mannide monooleate with paraffin oil in the proportions by volume of 1.5:8.5. The resulting vaccine is a water-in-oil emulsion with the antigen in the dispersed water phase. While the proportions of adjuvant to protein extract can vary considerably, approximately equal proportions are desirable.

The vaccines of this invention are particularly designed for use with cattle, and may be administered to calves and pregnant cattle. The vaccines can also be used with other bovine species, such as oxen or water buffalo. The volume of the injectable dose can vary, such as a volume of 1 to 4 ml. However, a 2 ml dose is convenient. In administering the vaccine, a single injection may be given but it is preferred to give two sequential injections per animal. For example, a 2 ml dose containing from 4 to 8 mg of total protein can be administered twice at 30 day intervals. The disease is prevented and the transfer of IBR virus by viral shed is also prevented, thereby more effectively controlling IBR infection.

In developing and testing the vaccines prepared in accordance with the present invention, the following materials and procedures were used.

VIRUS

The virulent Cooper strain of IBRV was received at the eighth passage level, from the National Veterinary Services Laboratory, Ames, Iowa. The Cooper strain is conventionally used as a challenge strain. It was passed two times in bovine lung cells (BLU) and a stock pool containing $1.0 \times 10^8$ plague forming units (PFU) per ml was frozen at $-70°$ C.

CELL CULTURE PROCEDURE

Cell cultures utilized in this study were grown in Eagle's minimum essential medium (MEM) supplemented with 10% irradiated fetal calf serum (FCS) (heat inactivated at 56° C. for 30 minutes), 0.5% lactalbumin hydrolysate and antibiotics (100 IU penicillin, 100 µg kanamycin sulfate and 100 µg streptomycin sulfate per ml). The medium was buffered with 0.16% sodium bicarbonate and 8 mM N-2-hydroxyethylpiperazine-N'-2-ethanesulfonic acid (HEPES). Culture were incubated at 37° C. in a 5% $CO_2$ atmosphere.

VIRUS ISOLATION

Nasal secretions were collected for virus isolation by insertion of a 15 cm cotton-tipped swab to its full length in the left ventral nasal meatus and manipulation of the swab in a rotary motion until saturated. Swab samples were immersed in 1.0 ml MEM containing antibiotics (200 IU penicillin, 200 µg kanamycin sulfate, 200 µg streptomycin sulfate and 15 µg amphoteracin B per ml) and held at 4° C. for 30 minutes. Swabs were then removed from the medium and the medium was frozen at $-70°$ C. until cultured.

Plague forming units of virus in specimens were determined by inoculation of duplicate cultures of BLU monolayers with serial 10-fold dilutions (in MEM) of each specimen. The inocula were adsorbed for 60 minutes, monolayers were washed with MEM and overlaid with 1% agarose containing MEM, 5% FCS and antibiotics. Cultures were incubated at 37° C. for 72 hours in a 5% $CO_2$ atmosphere. The cultures were fixed with 10% buffered formalin, the agarose layer was removed and the cell sheet was stained with crystal violet. The virus titer was determined by enumeration of PFUs.

PLAGUE REDUCTION-NEUTRALIZATION TESTS

Anti-IBR serum neturalization titers were determined by plague reduction-neutralization tests. Two-fold serum dilution of heat inactivated serum (56° C. for 30 minutes) were mixed with equal volumes of MEM containing 1000 PFU IBRV per ml and incubated for 60 minutes at 37° C. Monlayers of BLU cells in 35-mm 6-well plastic tissue culture plates were inoculated with 0.2 ml of serum-virus mixture. After adsorption of the serum-virus mixture for 60 minutes at 37° C., the cultures were washed with MEM, and overlaid with 1% agarose containing MEM, 5% FCS and antibiotics. Cultures were incubated at 37° C. for 72 hours and then fixed with 10% buffered formalin. The agarose layer was removed and the cell sheet was stained with crystal violet. The serum neutralization titer was the reciprocal of the highest serum dilution that reduced the plaque count by at least 50%.

PROTEIN DETERMINATION

Protein content was assayed by the method of Lowry et al, *J. Biol. Chem.*, 193, 265-275 (1951) with bovine serum albumin as the standard. Protein content of samples containing non-ionic detergent was determined using a modified Lowry procedure, as described in *Anal. Biochem.*, 86, 346-356 (1977).

Production of vaccines in accordance with the present invention and results obtained in the testing of the vaccines are illustrated by the following examples.

EXAMPLE I

Production of Vaccines

The bovine lung cells (BLU) were propagated in 490 $cm^2$ roller bottles until monolayers were formed. The monolayers were infected by removing the medium and adding 5 ml of stock IBRV, prepared as described above. After 60 minutes adsorption the inoculum was removed, the monolayer was washed with MEM and 30 ml of maintenance medium (MEM containing 5% FCS) was added. The cells were incubated at 37° C. with rolling (1 rpm) until cytopathic effect (CPE) was complete (approximately 24 hours). The infected BLU cells were scraped from the roller bottle surface with a rubber policeman. The cell-medium mixture was centrifuged at $100,000 \times g$ for 1 hour. The resultant pellet was solubilized using a modification of the procedure of Vestergaard et al, *J. Virol.*, 24, 87–90 (1977). The pellet was suspended in 0.010 M glycine-0.038 M tris (hydroxymethyl) aminomethane (Tris) (pH 9.0) containing 0.5% Triton X-100 (1 ml per roller bottle). The mixture was homogenized with a homogenizer and sonically treated for two-20 second cycles with a sonicator at a setting of 90% efficiency. The mixture was allowed to react for 1 hour at 4° C. with constant mixing by a magnetic stirrer. The mixture was centrifuged at 100,000×g for 1 hour and the supernatant harvested as the vaccine. The vaccine was stored at −70° C. until used. The vaccine was mixed with an equal volume of Freund's Complete or Freund's Incomplete Adjuvant and emulsified with 200 strokes in an adjuvant mixing apparatus. A second subunit vaccine was produced using a modification of the above procedure. The extracting solution was 2.5% Nonidet P-40 (NP-40) in distilled water prepared as described by Martin et al in *Infect. Immun.*, 5, 248–254 (1972).

EXAMPLE II

Determination of Vaccine Antigenicity

Triton X-100 solubilized IBR subunit vaccine and cell control preparations were administered to 10 IBR seronegative cattle in two intramuscular doses at 20 day intervals as detailed in Table A. Animals were observed daily throughout the study for clinical signs of disease. Rectal temperatures were recorded for 3 days prior to vaccination and for 10 days after vaccination. Nasal secretions were collected for virus isolation prior to vaccination and on days 2, 3 and 7 post-vaccination. Serum samples were collected at weekly intervals.

Experiment 1. Determination of subunit vaccine antigenicity

All 10 animals in this experiment remained clinically normal throughout the study. Rectal temperatures following vaccination were within ±1° C. of temperatures recorded prior to vaccination. Virus was not isolated from nasal secretions prior to or following vaccination. Serum neutralization titers are set out below in Table B.

TABLE A

Vaccination Schedule for Determination of Antigenicity of Triton X-100 Solubilized IBR Subunit Vaccine

| Calf Number | Vaccine | Dose (ml) Vaccination |
|---|---|---|
| 1 | Cell control without adjuvant | 1 |
| 2 | Cell control with adjuvant | 2 |
| 3 | IBR subunit without adjuvant | 1 |
| 4 | " | 1 |
| 5 | " | 2 |
| 6 | " | 2 |
| 7 | IBR subunit with adjuvant[1] | 2 |
| 8 | " | 2 |
| 9 | " | 4 |
| 10 | " | 4 |

[1]Freund's Complete Adjuvant.
[2]One ml without adjuvant and each 2 ml with adjuvant contained 4.4 mg of extracted protein.

TABLE B

Serum Neutralization Titers Following Intramuscular Administration of Triton X-100 Solubilized IBR Subunit Vaccine

| | | | Serum Neutralization Titer[1] Weeks Post Vaccination[3] | | | | | | |
|---|---|---|---|---|---|---|---|---|---|
| Calf Number | Vaccine | Dose (ml)[4] | 1 | 2 | 3 | 4 | 5 | 6 | 7 |
| 1 | Cell control without adjuvant | 1 | <2 | <2 | <2 | <2 | <2 | <2 | <2 |
| 2 | Cell control with adjuvant | 2 | <2 | <2 | <2 | <2 | <2 | <2 | <2 |
| 3 | IBR subunit without adjuvant | 1 | <2 | <2 | <2 | <2 | <2 | <2 | <2 |
| 4 | " | 1 | <2 | <2 | <2 | <2 | <2 | <2 | <2 |
| 5 | " | 2 | <2 | 8 | 4 | 8 | 2 | 2 | 2 |
| 6 | " | 2 | <2 | 4 | 4 | 8 | 8 | 8 | 4 |
| 7 | IBR subunit with adjuvant[2] | 2 | <2 | 4 | 8 | 128 | 128 | 128 | 128 |
| 8 | " | 2 | <2 | 8 | 16 | 1024 | 512 | 512 | 512 |
| 9 | " | 4 | <2 | 64 | 128 | 512 | 512 | 512 | 512 |
| 10 | " | 4 | <2 | 64 | 64 | 1024 | 1024 | 512 | 512 |

[1]Titer expressed as the reciprocal of the highest serum dilution that reduced the plaque count by at least 50%.
[2]Freund's Complete Adjuvant.
[3]Second dose of vaccine administered at 3 weeks.
[4]See Table A.

minutes post-challenge; 15 minute intervals thru 1 hour post-challenge; hourly intervals thru 15 hours post-challenge; at 18, 20, 22, 24 hours post-challenge; and at 24 hour intervals thru 14 days post-challenge. Serum samples were collected three times prior to vaccination and at weekly intervals following vaccination.

Following vaccination, 4 of 4 control calves and 5 of 12 vaccinates developed indurated swellings at the site of vaccine inoculation and febrile responses (40 to 41.1 C) that persisted for 1 to 3 days. Deep intramuscular inoculation and avoidance of "inoculum drag" prevented reaction to the second vaccination.

Table D summarizes the serum neutralization titers following vaccination and challenge.

Following intranasal challenge with IBRV, all calves in groups 2, 3, 4 and 5 remained clinically normal except calves 5, 10 and 11 which developed mild respiratory tract infection. Clinical signs of disease included elevated temperature, intranasal herpetic pustules and fibrino-necrotic nasal exudate. The clinical course of disease observed in calves 10 and 11 was characterized by an elevated temperature which persisted beyond resolution of intranasal lesions and nasal exudation. The temperature returned to base-line values 24 hours after antibiotic therapy was initiated on post-challenge day 9. Calf 20 died from causes unrelated to experimentation on post vaccination day 38. Post mortem examination

EXAMPLE III

Determination of Immune Protection

Twenty IBR seronegative calves, 3 to 6 months of age, were randomly divided into 5 groups (4 in each group) and housed in separate, enclosed, isolation rooms throughout the study. Groups of calves, designated 1 to 5, were vaccinated intramuscularly as detailed in Table C. Thirty days after vaccination, calves were administered a standard challenge virus inoculum ($1 \times 10^6$ PFU Cooper strain IBR, 10th passage). A gas-powered atomizer was used to deliver 2 ml of inoculum into each nostril.

Calves were examined daily for clinical signs of disease from 7 days prior to vaccination until the study was terminated. Rectal temperatures were recorded for 3 days prior to vaccination, for 10 days following each vaccination and for 14 days following challenge. Nasal secretions were collected for virus isolation three times prior to vaccination and daily for 7 days following the initial vaccination in each group. Following challenge, nasal secretions were collected at the following times: 5 did not reveal evidence of disease or any lesion at the site of vaccination. Challenge exposure of control calves produced a severe respiratory disease characterized by elevated temperature (to 41.7° C.) and formation of extensive fibrino-necrotic plaques on the nasal mucosa.

Virus was not recovered from nasal secretions prior to or following vaccination. In groups 2 and 3 challenge inoculum virus was isolated at 5 min and 15 min post challenge, but could not be isolated from nasal secretions of calves at 30 minutes after challenge exposure. Challenge inoculum virus could not be isolated from nasal secretions of calves in groups 4 and 5 minutes after challenge inoculum. Following the initial clearance of challenge virus inoculum, virus was isolated from nasal secretions 18 hours after challenge in groups 2 and 3 and at 22 hours in groups 4 and 5. Table E details shed of virus in nasal secretions for days 1 to 14 post challenge. Virus was not isolated from calves 13, 14, 17, 18, or 19 following intranasal challenge exposure.

TABLE C

Vaccination Schedule for Determination of Efficacy of Triton X-100 and NP-40 Solubilized IBR Subviral Vaccines

| Group Number | Calf Numbers | Vaccine | Doses of Vaccine[1] |
|---|---|---|---|
| 1 | 1 to 4 | Triton X-100 solubilized cell control | 1 |
| 2 | 5 to 8 | Triton X-100 IBR subunit | 1 |
| 3 | 9 to 12 | NP-40 IBR Subunit | 1 |
| 4 | 13 to 16 | Triton X-100 IBR subunit | 2 |
| 5 | 17 to 20 | NP-40 IBR Subunit | 2 |

[1]Each dose consisted of 1 ml cell extract and 1 ml Freund's Incomplete Adjuvant. Each ml of the Triton X-100 extract contained 3.5 mg protein, and for the NP-40 extract each ml contained 5.8 protein. The second dose of vaccine was administered at 30 days.

TABLE D:

Serum Neutralization Titers Following Intramuscular Administration of Triton X-100 and NP-40 Solubilized IBR Subviral Vaccine

| Group/Animal Number | Subunit Vaccine | Weeks post-vaccination — Serum neutralization titer[1] | | | | | | | | | Weeks post-Challenge[3] | |
|---|---|---|---|---|---|---|---|---|---|---|---|---|
| | | 0 | 1 | 2 | 3 | 4 | 5 | 6 | 7 | 8 | 1 | 2 |
| Group 1 | Control | | | | | | | | | | | |
| 1 | | <2 | <2 | <2 | <2 | <2 | | | | | <2 | 16 |
| 2 | | <2 | <2 | <2 | <2 | <2 | | | | | <2 | 32 |
| 3 | | <2 | <2 | <2 | <2 | <2 | | | | | <2 | 16 |
| 4 | | <2 | <2 | <2 | <2 | <2 | | | | | <2 | 32 |
| Group 2 | Triton X-100 1 dose | | | | | | | | | | | |
| 5 | | <2 | <2 | 16 | 16 | 32 | | Not Applicable | | | 128 | 512 |
| 6 | | <2 | 2 | 8 | 16 | 16 | | | | | 256 | 512 |
| 7 | | <2 | <2 | 8 | 16 | 16 | | | | | 32 | 512 |
| 8 | | <2 | 2 | 4 | 16 | 32 | | | | | 128 | 512 |
| Group 3 | NP-40 1 dose | | | | | | | | | | | |
| 9 | | <2 | 2 | 64 | 32 | 64 | | | | | 128 | 256 |
| 10 | | <2 | <2 | 32 | 32 | 64 | | | | | 128 | 512 |
| 11 | | <2 | 2 | 64 | 32 | 64 | | | | | 256 | 512 |
| 12 | | <2 | 4 | 64 | 32 | 64 | | | | | 256 | 1024 |
| Group 4 | Triton X-100 2 doses | | | | | | | | | | | |
| 13 | | <2 | 2 | 16 | 64 | 32 | 256 | 256 | 512 | 512 | 512 | 512 |
| 14 | | <2 | 2 | 16 | 32 | 64 | 1024 | 1024 | 512 | 1024 | 512 | 512 |
| 15 | | <2 | 2 | 8 | 8 | 8 | 256 | 256 | 128 | 128 | 64 | 256 |
| 16 | | <2 | 2 | 8 | 16 | 16 | 128 | 128 | 128 | 128 | 128 | 128 |
| Group 5 | NP-40 2 doses | | | | | | | | | | | |
| 17 | | <2 | 2 | 8 | 32 | 32 | 256 | 512 | 512 | 512 | 256 | 512 |
| 18 | | <2 | 2 | 8 | 64 | 64 | 256 | 256 | 256 | 256 | 256 | 512 |
| 19 | | <2 | <2 | 32 | 32 | 64 | 256 | 256 | 256 | 128 | 128 | 512 |
| 20 | | <2 | 2 | 16 | 16 | 16 | 128 | (2) | | | | 256 |

[1]Titer expressed as the reciprocal of the highest serum dilution that reduced plaque county by at least 50%
[2]Calf died on post-vaccination day 58
[3]Intranasal challenge with with $1 \times 10^6$ PFU Cooper stain IBR virus administered 30 days after last dose of vaccine

TABLE E:

Virus Isolation Following Intranasal Challenge of Calves Vaccinated with Triton X-100 and NP-40 Solubilized IBR Subviral Vaccine

| Group/Animal Number | Subunit Vaccine | Virus Titers[1] at Days Post Challenge | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 |
| Group 1 | Control | | | | | | | | | | | | | | |
| 1 | | 3.8 | 5.3 | 7.4 | 7.0 | 6.7 | 5.8 | 5.5 | 3.2 | 2.5 | —(2) | — | — | — | — |
| 2 | | 2.3 | 5.0 | 5.7 | 7.2 | 7.3 | 6.0 | 6.2 | 6.0 | 3.0 | — | — | — | — | — |
| 3 | | 3.0 | 4.8 | 6.8 | 6.3 | 5.9 | 4.0 | — | — | — | — | — | — | — | — |
| 4 | | 3.7 | 5.7 | 7.7 | 7.3 | 7.0 | 6.0 | 5.5 | 3.4 | 3.0 | — | — | — | — | — |
| Group 2 | Triton X-100 1 dose | | | | | | | | | | | | | | |
| 5 | | — | — | 3.0 | 5.0 | 5.8 | 4.7 | 5.9 | — | — | — | — | — | — | — |
| 6 | | — | 3.0 | 3.7 | 5.5 | 6.0 | 5.3 | 5.0 | — | — | — | — | — | — | — |
| 7 | | — | 2.3 | 2.3 | 4.2 | 6.7 | 5.6 | 5.8 | 4.0 | — | — | — | — | — | — |
| 8 | | — | — | — | — | 2.9 | 1.8 | 1.5 | — | — | — | — | — | — | — |
| Group 3 | NP-40 1 dose | | | | | | | | | | | | | | |
| 9 | | — | 1.0 | 4.6 | 4.8 | 5.0 | 3.2 | 4.3 | 2.5 | — | — | — | — | — | — |
| 10 | | — | — | 1.3 | 1.7 | 4.0 | 3.0 | 4.7 | 4.0 | 1.8 | — | — | — | — | — |
| 11 | | — | 1.0 | 3.4 | 4.7 | 5.2 | 4.5 | 4.5 | 1.6 | — | — | — | — | — | — |
| 12 | | 1.0 | 3.5 | 5.8 | 6.0 | 6.0 | 4.5 | 2.7 | — | — | — | — | — | — | — |
| Group 4 | Triton X-100 2 doses | | | | | | | | | | | | | | |
| 13 | | — | — | — | — | — | — | — | — | — | — | — | — | — | — |
| 14 | | — | — | — | — | — | — | — | — | — | — | — | — | — | — |
| 15 | | 1.5 | — | 2.3 | 2.9 | 3.7 | 4.6 | 5.6 | 4.8 | 3.0 | 2.9 | — | — | — | — |
| 16 | | 1.9 | 1.2 | 1.6 | 2.6 | 1.5 | — | — | — | — | — | — | — | — | — |
| Group 5 | NP-40 2 doses | | | | | | | | | | | | | | |
| 17 | | — | — | — | — | — | — | — | — | — | — | — | — | — | — |
| 18 | | — | — | — | — | — | — | — | — | — | — | — | — | — | — |

TABLE E:-continued

Virus Isolation Following Intranasal Challenge of Calves Vaccinated with Triton X-100 and NP-40 Solubilized IBR Subviral Vaccine

| Group/Animal Number | Subunit Vaccine | Virus Titers[1] at Days Post Challenge | | | | | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 |
| | | — | — | — | — | — | — | — | — | — | — | — | — | — | — |

[1] Virus titer as $\log_{10}$ plaque forming units/nasal swab
[2] No virus detected where no values shown As used herein, reference to "prevention of IBR disease" means that the vaccine protects bovines against development of clinical signs of the disease when challenged with virulent IBR virus. In cattle a principle clinical sign of the disease is a temperature elevation to 103.5° F. or higher for two or more days. Vaccinated cattle after challenge, although not evidencing any clinical signs of the disease, may shed virulent IBR virus, which can transfer infection to other non-vaccinated cattle. Therefore, when reference is made herein to "prevention of IBR infection", this means that the vaccine also prevents virus shed, as well as preventing the disease. This result is new and surprising.

We claim:

1. A parenteral vaccine in injectable dose form for prevention in bovines of infectious bovine rhinotracheitis (IBR), characterized by containing an effective IBR disease-preventing amount of IBR viral envelope protein, said viral envelope protein having been obtained by propagating virulent IBR virus in a cell culture medium containing growing cells capable of promoting the multiplication of said virus, said IBR viral envelope protein collecting on the membranes of said cells during said propagation, separating the infected cells from the mixture, contacting the cellular membranes of the separated cells with an aqueous solution of a non-ionic detergent to obtain an aqueous solution of said viral envelope protein, and separating said aqueous solution containing the solubilized viral envelope protein from the non-solubilized residue.

2. Th parenteral vaccines of claim 1 in which said injectable dose contains an adjuvant for promoting the immunogenic response of bovines to said viral envelope protein.

3. A parenteral vaccine in injectable dose form for immunizing cattle against infectious bovine rhinotracheitis (IBR), and for preventing transfer of IBR infective virus, comprising an aqueous solution of IBR viral envelope protein in admixture with a water-immiscible oil adjuvant, said vaccine dose containing an effective amount of said viral envelope for IBR immunization and prevention of IBR virus shed by sequential administration of two of said doses per animal, said viral envelope protein having been obtained by propagating virulent IBR virus in a cell culture medium containing growing bovine cells capable of promoting the multiplication of said virus, said IBR viral envelope protein collecting on the membranes of said cells during said propagation, separating the infected cells from the mixture, contacting the cellular membranes of the separated cells with an aqueous solution of a non-ionic detergent to obtain an aqueous solution of said viral envelope protein, and separating said aqueous solution containing the solubilized viral envelope protein from the non-solubilized residue said vaccine being free of said virulent IBR virus.

4. The parenteral vaccine of claim 3 in which said separated aqueous solution of subunit protein is used in said vaccine without concentration of the protein therein.

5. The parenteral vaccine of claim 3 or claim 4 in which each of said doses has a volume of substantially two milliliters and each dose contains from 4 to 8 milligrams of total protein.

6. The method of preventing infection of cattle by infectious bovine rhinotracheitis virus (IBR virus) and transfer of IBR virus by virus shed, comprising parenterally administering at least two successive doses of a vaccine conan effective disease-preventing amount of IBR viral envelope protein, said viral envelope protein having been obtained by propagating virulent IBR virus in a cell culture medium containing growing bovine cells capable of promoting the multiplication of said virus, said IBR viral envelope protein collecting on the membranes of said cells during said propagation, separating the infected cells from the mixture, contacting the cellular membranes of the separated cells with an aqueous solution of a non-ionic detergent to obtain an aqueous solution of said viral envelope protein, and separating said aqueous solution containing the solubilized viral envelope protein from the non-solubilized residue, said vaccine being free of virulent IBR virus.

7. The method of claim 6 in which said vaccine contains an adjuvant for promoting the immunogenic response.

8. The method of claim 6 or claim 7 in which each of said doses contains from 4 to 8 milligrams of total protein.

* * * * *

UNITED STATES PATENT OFFICE
CERTIFICATE OF CORRECTION

Patent No. 4,291,019          Dated September 22, 1981

Inventor(s) Harold W. Lupton and David E. Reed

It is certified that error appears in the above-identified patent and that said Letters Patent are hereby corrected as shown below:

In Claim 6, line 34, cancel "conan" and substitute "containing an".

Signed and Sealed this

Eighth Day of December 1981

[SEAL]

Attest:

Attesting Officer

GERALD J. MOSSINGHOFF
Commissioner of Patents and Trademarks